United States Patent
Adolf et al.

(10) Patent No.: US 7,361,347 B2
(45) Date of Patent: Apr. 22, 2008

(54) CYTOTOXIC CD44 ANTIBODY IMMUNOCONJUGATES

(75) Inventors: Guenther Adolf, Vienna (AT); Erik Patzelt, Purkersdorf (AT); Marlies Sproll, Gauting (DE); Karl-Heinz Heider, Stockerau (AT)

(73) Assignee: Boehringer Ingelheim International GmbH, Ingelheim (DE)

( * ) Notice: Subject to any disclaimer, the term of this patent is extended or adjusted under 35 U.S.C. 154(b) by 152 days.

(21) Appl. No.: 11/173,969

(22) Filed: Jul. 1, 2005

(65) Prior Publication Data

US 2005/0271672 A1    Dec. 8, 2005

Related U.S. Application Data

(63) Continuation of application No. 10/150,475, filed on May 17, 2002, now abandoned.

(60) Provisional application No. 60/307,451, filed on Jul. 24, 2001.

(30) Foreign Application Priority Data

May 18, 2001    (EP)    ................... 01112227

(51) Int. Cl.
    *A61K 39/395*    (2006.01)
(52) U.S. Cl. ............... 424/181.1; 424/178.1; 424/179.1; 530/391.1; 530/391.7
(58) Field of Classification Search ............ None
    See application file for complete search history.

(56) References Cited

U.S. PATENT DOCUMENTS

| | | | |
|---|---|---|---|
| 5,208,020 | A | 5/1993 | Chari et al. |
| 5,916,561 | A | 6/1999 | Adolf et al. |
| 6,323,334 | B1 | 11/2001 | Kingsbury et al. |
| 2004/0126379 | A1 | 7/2004 | Adolf et al. |

FOREIGN PATENT DOCUMENTS

| | | | |
|---|---|---|---|
| EP | 0 425 235 | A | 5/1991 |
| WO | WO 97 21104 | A | 6/1997 |
| WO | WO 98 22508 | A | 5/1998 |
| WO | WO 98 39034 | A | 9/1998 |
| WO | WO 01 00244 | A | 1/2001 |
| WO | WO 01/24763 | A2 | 4/2001 |

OTHER PUBLICATIONS

Minuno et al Drug Delivery System vol. 11 p. 385 (1996).*
Muzino et al, Drug Delivery Syst. vol. 11 No. 6 p. 385-391 (1996).*
Fowers, K. et al: "Targeting of HPMA copolymer-drug conjugates to A2780/AD ovarian cancer cells using anti-P-glycoprotein antibodies or fragments"; Proc. 25th Int. Symp. Controlled Release Bioact. Mater, (1999), 527-528.

Wu, M. et al: "Potent deglycosylated ricin A chain immunotoxins specific killing of xenotropic murine retrovirus-Infected cells";Chin. Med. J., (1994) 107(5):383-385.
Eliaz, R. E. et al: "Liposome-encapsulated doxorubicin targeted to CD44: a strategy to kill CD44-overexpressing tumor cells"; Cancer Res., (2001), 61(6):2592-2601.
Csanaky, G. et al: "Adhesion receptors on peripheral blood leukemic B cells. A comparative study on B cell chronic lymphocytic leukemia and related lymphoma/leukemias"; Leukemia (1997), 11(3):408-15.
Lesley, J. et al: "Binding of hyaluronic acid to lymphoid cell lines is inhibited by monoclonal antibodies against Pgp-1"; Experimental Cell Research (1990), 187(2):224-33.
Guo, Y. et al: "Inhibition of human melanoma growth and metastasis in vivo by anti-CD44 monoclonal antibody", Cancer Research (1994), 54(6):1561-5.
Heider, K-H et al: "Splice Variants of the Cell Surface Glycoprotein CD44 Associated with Metastatic Tumour Cells are Expressed in Normal Tissues of Humans and Cynomolgus Monkeys"; European J. of Cancer (1995) 31A (13/14):2385-2391, Pergamon Press, Oxford, GB.
Heider, K-H et al: "Characterization of A High-Affinity Monoclonal Antibody Specific for CD44V6 as Candidate for Immunotherapy of Squamous Cell Carcinomas"; Cancer Immunology and Immunotherapy, (1996), 43:245-253.
Chari R V J et al: "Immunoconjugates containing novel maytansinoids: Pormising Anticancer Drugs"; Cancer Research, American Association for Cancer Research, (1992), 52(1):127-131, Baltimore MD, US.
Liu, C. et al: "The development of antibody delivery systems to target cancer with highly potent maytansinoids"; Expert Opin. Invest. Drugs (1997), 6(2):169-172.
Liu, C. et al: "Eradication of large colon tumor xenografts by targeted delivery of maytansinoids" Proc. Natl. Acad. Sci. U.S.A., (1996), 93(16):8618-8623.
Verel I. et al: "Tumor Targeting Properties of Monoclonal Antibodies with Different Affinity for Target Antigen CD44V6 In Nude Mice Bearing Head-And-Neck Cancer Xenografts"; Int. J. Cancer (2002), 99:396-402.
Newton, D. et al: "Anti-tumor ribonuclease, combined with or conjugated to monoclonal antibody MRK16, overcomes multidrug resistance to vincristine in vitro and in vivo." Int. J. of Oncology (1996), 8:1095-1104.
Liu, C. et al: "Cure of large human colon cancer xenografts by a C242-Maytansinoid conjugate." Proceedings of the American Assoc. for Cancer Res. Annual; 1996, 37:466-467, abst. #3183.

(Continued)

*Primary Examiner*—Sheela J. Huff
(74) *Attorney, Agent, or Firm*—Michael P. Morris; Mary-Ellen M. Devlin

(57) ABSTRACT

The invention relates to novel conjugates of CD44 antibodies with cytotoxic compounds, pharmaceutical compositions comprising such compounds, and their use in tumor therapy.

21 Claims, 5 Drawing Sheets

OTHER PUBLICATIONS

Figure 1:
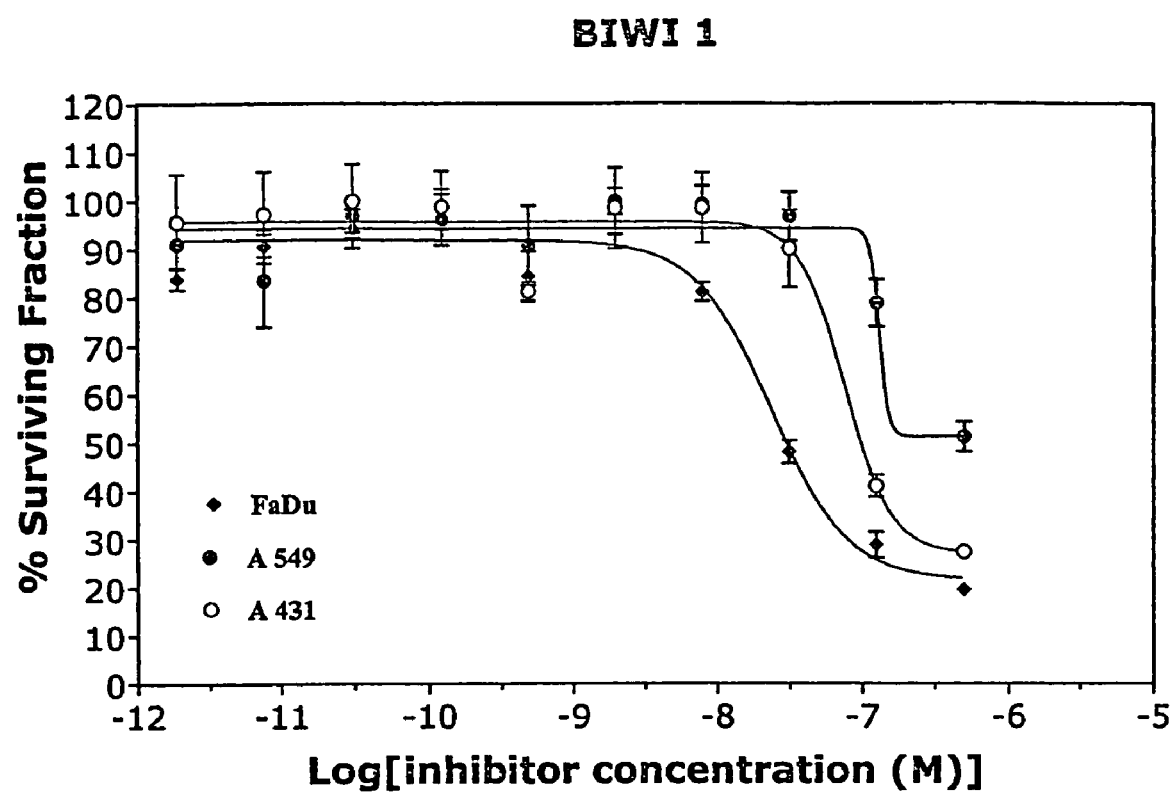

Smith, S.: "Technology evaluation: c242-DM1, ImmunoGen Inc.," Current Opinion in Molecular Therapeutics; 2001, 3(2):198-203.
Somasundaram, C. et al: " Development of a bispecific F(ab')2 conjugate against the complement receptor cr3 of macrophages and a variant cd44 antigen of rat pancreatic adenenocarcinoma for redirecting macrophage-mediated tumor cytotoxity"; Cancer Immunology and Immunotherapy, 1996, 42(6):343-350.
Monneret C. et al: "Ciblage de molecules antitumorales par les anticorps monoclonaux." Bulletin Du Cancer; 2000, 87(11)829-838.

* cited by examiner

SEQUENCE LISTING

```
<160> NUMBER OF SEQ ID NOS: 9

<210> SEQ ID NO 1
<211> LENGTH: 42
<212> TYPE: PRT
<213> ORGANISM: Homo sapiens
<220> FEATURE:
<223> OTHER INFORMATION: Description of Artificial Sequence: Human CD44
      Exon v6 SEQ ID NO: 1

<400> SEQUENCE: 1

Gln Ala Thr Pro Ser Ser Thr Thr Glu Glu Thr Ala Thr Gln Lys Glu
  1               5                  10                  15

Gln Trp Phe Gly Asn Arg Trp His Glu Gly Tyr Arg Gln Thr Pro Arg
                 20                  25                  30

Glu Asp Ser His Ser Thr Thr Gly Thr Ala
             35                  40

<210> SEQ ID NO 2
<211> LENGTH: 14
<212> TYPE: PRT
<213> ORGANISM: Homo sapiens
<220> FEATURE:
<223> OTHER INFORMATION: Description of Artificial Sequence:
      SEQ ID NO: 2

<400> SEQUENCE: 2

Gln Trp Phe Gly Asn Arg Trp His Glu Gly Tyr Arg Gln Thr
  1               5                  10

<210> SEQ ID NO 3
<211> LENGTH: 11
<212> TYPE: PRT
<213> ORGANISM: Homo sapiens
<220> FEATURE:
<223> OTHER INFORMATION: Description of Artificial Sequence:
      SEQ ID NO: 3

<400> SEQUENCE: 3

Trp Phe Gly Asn Arg Trp His Glu Gly Tyr Arg
  1               5                  10

<210> SEQ ID NO 4
<211> LENGTH: 213
<212> TYPE: PRT
<213> ORGANISM: Artificial Sequence
<220> FEATURE:
<223> OTHER INFORMATION: Description of Artificial Sequence: Humanised
      Murine Antibody BIWA 4 Light Chain SEQ ID NO: 4

<400> SEQUENCE: 4

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Ile Asn Tyr Ile
                 20                  25                  30

Tyr Trp Tyr Gln Gln Lys Pro Gly Gln Ala Pro Arg Leu Leu Ile Tyr
                 35                  40                  45

Leu Thr Ser Asn Leu Ala Ser Gly Val Pro Ala Arg Phe Ser Gly Ser
             50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Leu Gln Trp Ser Ser Asn Pro Leu Thr
```

```
                    85                  90                  95
Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 5
<211> LENGTH: 702
<212> TYPE: DNA
<213> ORGANISM: Artificial Sequence
<220> FEATURE:
<223> OTHER INFORMATION: Description of Artificial Sequence: Humanised
      Murine Antibody BIWA 4 Light Chain SEQ ID NO: 5

<400> SEQUENCE: 5
atggaagccc cagctcagct tctcttcctc ctgctgctct ggctcccaga taccaccgga      60
gaaattgttc tcacccagtc tccagcaacc ctgtctctgt ctccagggga gagggccacc     120
ctgtcctgca gtgccagctc aagtataaat tacatatact ggtaccagca gaagccagga     180
caggctccta gactcttgat ttatctcaca tccaacctgg cttctggagt ccctgcgcgc     240
ttcagtggca gtgggtctgg aaccgacttc actctcacaa tcagcagcct ggagcctgaa     300
gattttgccg tttattactg cctgcagtgg agtagtaacc cgctcacatt cggtggtggg     360
accaaggtgg agattaaacg tacggtggct gcaccatctg tcttcatctt cccgccatct     420
gatgagcagt tgaaatctgg aactgcctct gttgtgtgcc tgctgaataa cttctatccc     480
agagaggcca agtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ga                       702

<210> SEQ ID NO 6
<211> LENGTH: 444
<212> TYPE: PRT
<213> ORGANISM: Artificial Sequence
<220> FEATURE:
<223> OTHER INFORMATION: Description of Artificial Sequence: Humanised
      Murine Antibody BIWA 4 Heavy Chain SEQ ID NO: 6

<400> SEQUENCE: 6

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Gly Leu Glu Trp Val
```

```
                    35                  40                  45
Ser Thr Ile Ser Ser Gly Gly Ser Tyr Thr Tyr Leu Asp Ser Ile
     50                   55                  60

Lys Gly Arg Phe Thr Ile Ser Arg Asp Asn Ala Lys Asn Ser Leu Tyr
 65                   70                  75                  80

Leu Gln Met Asn Ser Leu Arg Ala Glu Asp Thr Ala Val Tyr Tyr Cys
                 85                  90                  95

Ala Arg Gln Gly Leu Asp Tyr Trp Gly Arg Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 7
```

<211> LENGTH: 1392
<212> TYPE: DNA
<213> ORGANISM: Artificial Sequence
<220> FEATURE:
<223> OTHER INFORMATION: Description of Artificial Sequence: Humanised
      Murine Antibody BIWA 4 Heavy Chain SEQ ID NO: 7

<400> SEQUENCE: 7

```
atggagtttg ggctgagctg gcttttctt  gtggctattt taaaaggtgt ccagtgtgaa    60
gtgcagctgg tggagtctgg gggaggctta gtgaagcctg agggtccct  aagactctcc   120
tgtgcagcct ctggattcac tttcagtagc tatgacatgt cttgggttcg ccaggctccg   180
gggaaggggc tggagtgggt ctcaaccatt agtagtggtg gtagttacac ctactatcta   240
gacagtataa agggccgatt caccatctcc agagacaatg ccaagaactc cctgtacctg   300
caaatgaaca gtctgagggc tgaggacacg gccgtgtatt actgtgcaag acaggggttg   360
gactactggg gtcgaggaac cttagtcacc gtctcctcag ctagcaccaa ggcccatcg    420
gtcttccccc tggcaccctc ctccaagagc acctctgggg gcacagcggc cctgggctgc   480
ctggtcaagg actacttccc cgaaccggtg acggtgtcgt ggaactcagg cgccctgacc   540
agcggcgtgc acaccttccc ggctgtccta cagtcctcag gactctactc cctcagcagc   600
gtggtgaccg tgccctccag cagcttgggc acccagacct acatctgcaa cgtgaatcac   660
aagcccagca acaccaaggt ggacaagaaa gttgagccca atcttgtga  caaaactcac   720
acatgcccac cgtgcccagc acctgaactc ctggggggac cgtcagtctt cctcttcccc   780
ccaaaaccca aggacaccct catgatctcc cggacccctg aggtcacatg cgtggtggtg   840
gacgtgagcc acgaagaccc tgaggtcaag ttcaactggt acgtggacgg cgtggaggtg   900
cataatgcca agacaaagcc gcgggaggag cagtacaaca gcacgtaccg tgtggtcagc   960
gtcctcaccg tcctgcacca ggactggctg aatggcaagg agtacaagtg caaggtctcc  1020
aacaaagccc tcccagcccc catcgagaaa accatctcca aagccaaagg cagccccga   1080
gaaccacagg tgtacaccct gcccccatcc cgggatgagc tgaccaagaa ccaggtcagc  1140
ctgacctgcc tggtcaaagg cttctatccc agcgacatcg ccgtggagtg ggagagcaat  1200
gggcagccgg agaacaacta caagaccacg cctcccgtgc tggactccga cggctccttc  1260
ttcctctaca gcaagctcac cgtggacaag agcaggtggc agcaggggaa cgtcttctca  1320
tgctccgtga tgcatgaggc tctgcacaac cactacacgc agaagagcct ctccctgtct  1380
ccgggtaaat ga                                                      1392
```

<210> SEQ ID NO 8
<211> LENGTH: 213
<212> TYPE: PRT
<213> ORGANISM: Artificial Sequence
<220> FEATURE:
<223> OTHER INFORMATION: Description of Artificial Sequence: Humanised
      Murine Antibody BIWA 8 Light Chain SEQ ID NO: 8

<400> SEQUENCE: 8

```
Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Ile Asn Tyr Ile
                 20                  25                  30

Tyr Trp Leu Gln Gln Lys Pro Gly Gln Ala Pro Arg Ile Leu Ile Tyr
             35                  40                  45

Leu Thr Ser Asn Leu Ala Ser Gly Val Pro Ala Arg Phe Ser Gly Ser
         50                  55                  60
```

```
Gly Ser Gly Thr Asp Phe Thr Leu Thr Ile Ser Ser Leu Glu Pro Glu
 65                  70                  75                  80

Asp Phe Ala Val Tyr Tyr Cys Leu Gln Trp Ser Ser Asn Pro Leu Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 9
<211> LENGTH: 702
<212> TYPE: DNA
<213> ORGANISM: Artificial Sequence
<220> FEATURE:
<223> OTHER INFORMATION: Description of Artificial Sequence: Humanised
      Murine Antibody BIWA 8 Light Chain SEQ ID NO: 9

<400> SEQUENCE: 9

```
atggaagccc agctcagct  tctcttcctc ctgctgctct ggctcccaga taccaccgga     60
gaaattgttc tcacccagtc tccagcaacc ctgtctctgt ctccagggga gagggccacc    120
ctgtcctgca gtgccagctc aagtataaat tacatatact ggctccagca gaagccagga    180
caggctccta gaatcttgat ttatctcaca tccaacctgg cttctggagt ccctgcgcgc    240
ttcagtggca gtgggtctgg aaccgacttc actctcacaa tcagcagcct ggagcctgaa    300
gattttgccg tttattactg cctgcagtgg agtagtaacc cgctcacatt cggtggtggg    360
accaaggtgg agattaaacg tacggtggct gcaccatctg tcttcatctt cccgccatct    420
gatgagcagt tgaaatctgg aactgcctct gttgtgtgcc tgctgaataa cttctatccc    480
agagaggcca agtacagtg  gaaggtggat aacgccctcc aatcgggtaa ctcccaggag    540
agtgtcacag agcaggacag caaggacagc acctacagcc tcagcagcac cctgacgctg    600
agcaaagcag actacgagaa acacaaagtc tacgcctgcg aagtcaccca tcagggcctg    660
agctcgcccg tcacaaagag cttcaacagg ggagagtgtt ga                       702
```

CYTOTOXIC CD44 ANTIBODY IMMUNOCONJUGATES

CROSS REFERENCE TO RELATED APPLICATIONS

This application in a continuation application of U.S. patent application Ser. No. 10/150,475, filed May 17, 2002, now abandoned and entitled "Cytotoxic CD44 Antibody Immunoconjugates," the entire disclosure of which is hereby incorporated by reference, which claims the benefit of U.S. Provisional Application No. 60/307,451, filed Jul. 24, 2001, the entire disclosure of which is hereby incorporated by reference.

BACKGROUND

The invention relates to novel conjugates of antibodies with cytotoxic compounds, pharmaceutical compositions comprising such compounds, and their use in tumor therapy.

There have been numerous attempts to improve the efficacy of antineoplastic drugs by conjugating such drugs to antibodies against tumor-associated antigens in order to elevate local concentration of the drug by targeted delivery to the tumor. Many of these approaches have met limited success, and several reasons have been discussed in the literature to explain the failure. For anticancer drugs acting stoichometrically, like e.g. doxorubicin or methotrexate, relatively high intracellular concentrations are necessary to exert the required cytotoxicity. These concentrations are thought to be difficult to achieve with many antibody-drug conjugates because of (a) insufficient potency of many common anticancer drugs, (b) low cell surface concentration of antigen targets, (c) inefficient internalization of antigen-antibody complexes into the target cell, and (d) inefficient release of free drug from the conjugate inside the target cell (Chari R V J et al. Cancer Research 52:127-31, 1992).

Two of the aforementioned drawbacks, namely (a) and (d), have been adressed by the work of Chari and coworkers (Chari R V J et al. Cancer Research 52:127-31, 1992; Liu C. et al. Proc Natl Acad Sci USA 93:8618-23, 1996; U.S. Pat. No. 5,208,020). They have developed antibody conjugates wherein the antibody is linked to a maytansinoid via a disulfide linkage. Maytansines belong to the class of Ansa macrolide antibiotics, which derive from *Nocardia* sp. The maytansine ansamitocin P-3, produced by bacterial fermentation, is used as a precursor molecule to manufacture maytansinoid DM1. Maytansine and derivatives act as anti-mitotic agents (inhibitors of tubulin polymerization), similar as vincristine, but with markedly higher potency than vincristine or other established chemotherapeutic agents (DM1 is toxic to cells in vitro at approximately $10^{-10}$ M concentration). In contrast to the high cytotoxicity of free maytansinoid, the antibody conjugate has a toxicity which is several orders of magnitude lower on antigen-negative cells compared to antigen-positive cells. The linkage by disulfide bonding has the advantage that these bonds are readily cleaved inside the target cells by intracellular glutathione, releasing highly toxic free drug. This approach has been applied to antibodies against tumor-associated antigens, for example the C242-DM1 conjugate (Liu C. et al. Proc Natl Acad Sci USA 93:8618-23, 1996; Lambert J M et al. American Association of Cancer Research 39: Abs 3550, 1998), and HuN901-DM1 (Chari R V J et al. Amerian Association of Cancer Research 41 (April 1-5) Abs 4405, 2000). However, the application of these conjugates is restricted due to the limited expression of the respective target antigens. For example, the antigen recognized by N901 (CD56, N-CAM) is predominanttly expressed by tumors of neuroendocrine origin, the expression of the C242 antigen (CanAg) is mostly limited to tumors derived from the GI tract.

There is, however, still the need to improve this approach by finding suitable tumor-associated antibodies with favorable antigen expression pattern, high and specific cell surface antigen concentration within the target tissue, and efficient internalization process transporting the antigen complexed-antibody conjugate into the cells.

CD44 is a protein which is expressed in several different isoforms on the surface of a wide variety of cell types. The smallest isoform, standard CD44 (CD44s), which is expressed by a variety of different cells, is thought to mediate cell attachment to extracellular matrix components and may transmit a co-stimulus in lymphocyte and monocyte activation. In contrast, expression of splice variants of CD44 which contain the domain v6 (CD44v6) in the extracellular region, is restricted to a subset of epithelia. The physiological role of CD44v6 is not yet fully understood.

CD44v6, as well as other variant exons (CD44v3, CD44v5, CD44v7/v8, CD44v10) has been shown to be a tumor-associated antigen with a favorable expression pattern in human tumors and normal tissues (Heider K H et al. Eur. J. Cancer 31A:2385-2391, 1995; Heider K H et al. Cancer Immunology Immunotherapy 43:245-253, 1996; Dall et al., 1996; Beham-Schmid et al., 1998; Tempfer et al., 1998; Wagner et al., 1998) and has been subject to antibody-based diagnostic and therapeutic approaches, in particular radioimmunotherapy (RIT) of tumors (Stroomer J W et al. Clin Cancer Res 6(8):3046-55, 2000, WO 95/33771, WO 97/21104).

However, a prerequisite for efficient killing of tumor cells by antibody maytansinoid conjugates is sufficient internalization of the target antigen. Only few data on the internalization of CD44 are available. Bazil and Horejsi reported that downregulation of CD44 on leukocytes upon stimulation with PMA is caused by shedding of the antigen rather than by internalization (Bazil V. and Horejsi V. J. Immunol. 149 (3):747-753, 1992). Shedding of CD44 is also supported by several reports on soluble CD44 in the serum of tumor patients and normal individuals (Sliutz G et al. Br. J. Cancer 72:1494-1497, 1995; Guo Y J et al. Cancer Research 54(2): 422-426, 1994; Martin S. et al. Int J Cancer 74(4):443-445, 1997). In a recent paper by Aguiar et al. the amount of internalized CD44 on matrix-intact chondrocytes was determined to be approximately 6% in 4 hours (Aguiar D J, et al., Exp. Cell. Res. 252:292-302, 1999). Similar low levels of internalized CD44v6 on tumor cells were found in experiments performed by BIA. Taken together, these data suggest that CD44 receptors are more likely subject to shedding than to internalization, and thus CD44 specific antibodies are not to be regarded as suitable candidates for the maytansinoid conjugate approach. This has been supported by in vitro cell proliferation assays wherein $Ab_{CD44v6}$-DM1 showed only slightly elevated cytotoxicity against antigen-presenting cells as compared to cells lacking the antigen.

It now has been unexpectedly found that CD44 specific antibodies conjugated to highly cytotoxic drugs through a linker which is cleaved under intracellular conditions are very efficient tumor therapeutics in vivo.

SUMMARY

The invention relates to novel conjugates of CD44 antibodies with cytotoxic compounds, pharmaceutical compositions comprising such compounds, and their use in tumor therapy. In particular, the present invention provides a compound of formula: $A(LB)_n$ (Formula (I)) wherein A is an antibody molecule which is specific for CD44; L is a linker moiety; B is a compound which is toxic to cells; and n is a decimal number with n=1 to 10. In a preferred embodiment, the antibody specifically binds a variant of CD44. In another preferred embodiment, the toxic compound (B) is a maytansinoid.

FIGURES

FIG. 1: In vitro cytotoxicity of BIWI 1. The antigen-positive cell lines A431 and FaDu and the antigen-negative cell line A549 were used.

Figure 2:
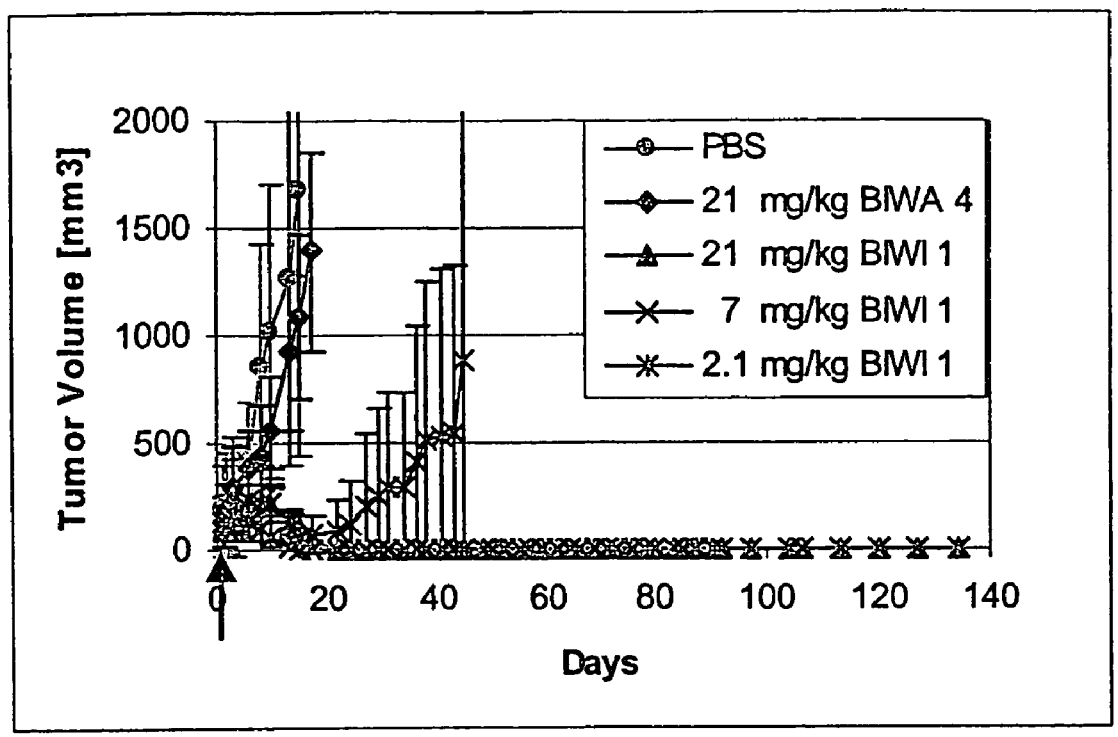

FIG. 2: Efficacy of BIWI 1 treatment in nude mice xenografted with A431 tumors. The average tumor volumes per group with standard deviations are shown, the treatment groups are indicated. The arrow indicates start of treatment (day 1).

Figure 3:
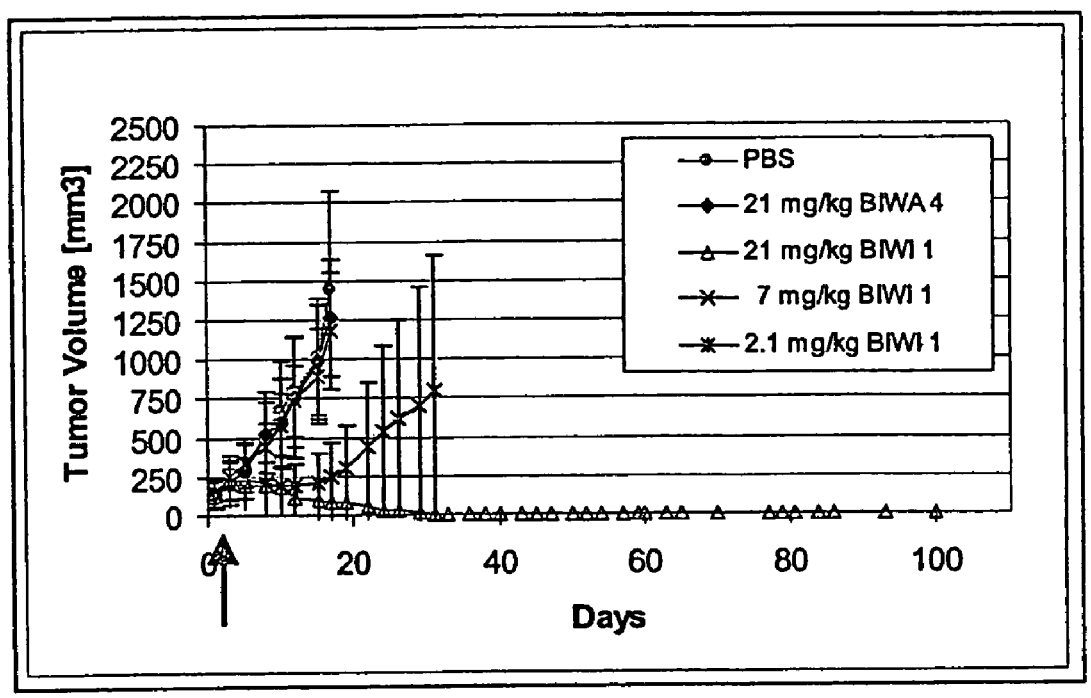

FIG. 3: Efficacy of BIWI 1 treatment in nude mice xenografted with FaDu tumors. The average tumor volumes per group with standard deviations are shown, the treatment groups are indicated. The arrow indicates start of treatment (day 1).

Figure 4:
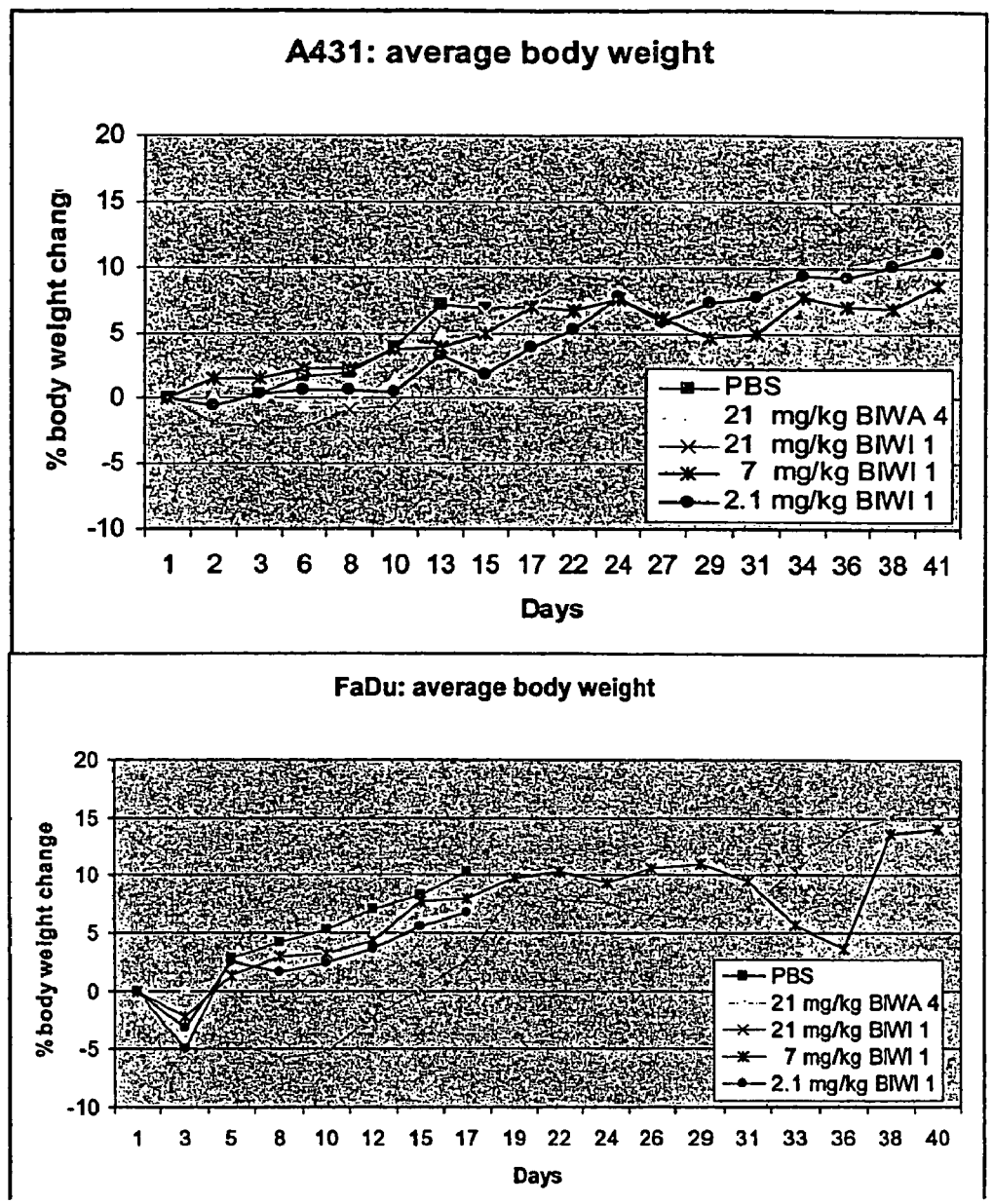

FIG. 4: Tolerability of BIWI 1 treatment. The average body weight change of all treatment groups in the 2 investigated models is shown. Day 1: start of treatment.

Figure 5:
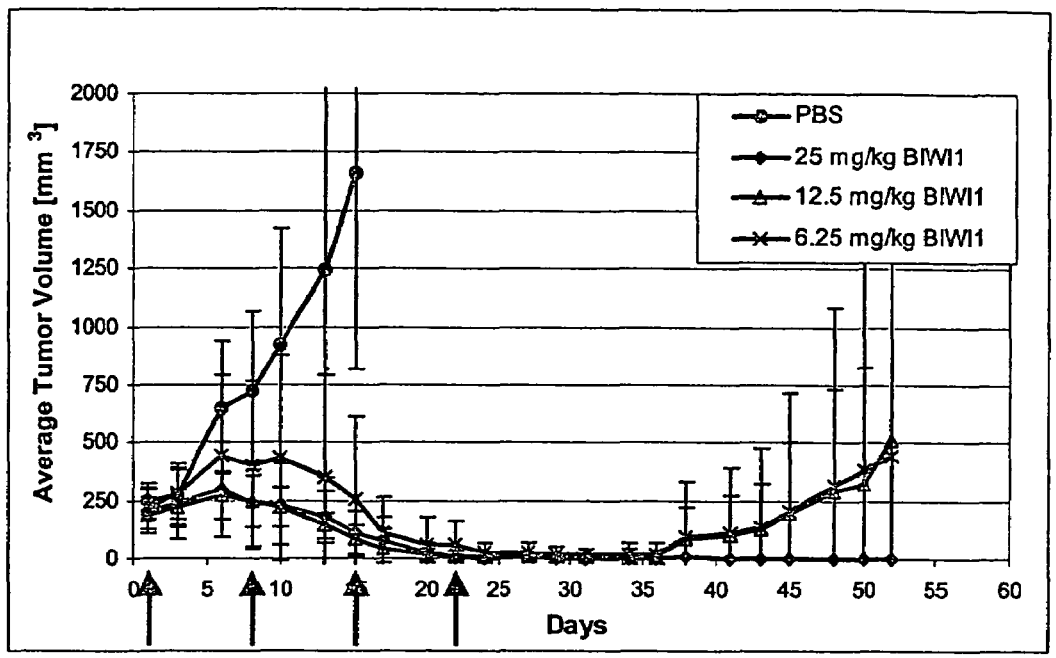

FIG. 5: Efficacy of BIWI 1 treatment in nude mice xenografted with MDA-MB 453 tumors. The average tumor volumes per group with standard deviations are shown, the treatment groups are indicated. The arrows indicate the treatment days.

DETAILED DESCRIPTION OF THE INVENTION

The present invention provides novel compounds consisting of a CD44 specific antibody molecule conjugated to a highly cytotoxic drug through a linker which is cleaved under intracellular conditions.

In particular, the present invention provides a compound of formula $$A(LB)_n \qquad \text{(Formula (I))}$$

wherein
A is an antibody molecule which is specific for CD44;
L is a linker moiety;
B is a compound which is toxic to cells; and
n is a decimal number with n=1 to 10

The antibody molecule A has a binding specificity for CD44, preferably variant CD44. The term "antibody molecule" shall encompass complete immunoglobulins as they are produced by lymphocytes and for example present in blood sera, monoclonal antibodies secreted by hybridoma cell lines, polypeptides produced by recombinant expression in host cells which have the binding specificity of immunoglobulins or monoclonal antibodies, and molecules which have been derived from such immunoglobulins, monoclonal antibodies, or polypeptides by further processing while retaining their binding specificity. In particular, the term "antibody molecule" includes complete immunoglobulins comprising two heavy chains and two light chains, fragments of such immunoglobulins like Fab, Fab', or F(ab)$_2$ fragments (Kreitman R J et al. Cancer Res. 53:819-825, 1993), recombinantly produced polypeptides like chimeric, humanised or fully human antibodies (Breitling F. and Duebel S., John Wiley, New York 1999; Shin S-U et al. Methods Enzymol. 178:459-476, 1989; Güssow D and Seemann G, Methods Enzymol. 203:99-121, 1991, Winter, G. et al. Ann. Rev. Immunol. 12:433-455, 1994, EP 0 239 400; EP 0 519 596; WO 90/07861 EP 0 368 684; EP 0 438 310; WO 92/07075; WO 92/22653; EP 0 680 040; EP 0 451 216), single chain antibodies (scFv, Johnson and Bird, Methods Enzymol. 203:88-98, 1991), and the like. Today, antibodies may also be produced without immunising a laboratory animal, e.g. by phage display methods (Aujame L., et al. Hum Antibodies 8(4):155-68, 1997; U.S. Pat. Nos. 5,885, 793; 5,969,108; 6,300,064; 6,248,516, 6,291,158). Fully human antibodies may be produced using transgenic mice carrying functional human Ig genes (EP 0 438 474; EP 0 463 151; EP 0 546 073). From the aforementioned literature references, the expert knows how to produce these types of antibody molecules, employing state of the art methods like automated peptide and nucleic acid synthesis, laboratory animal immunisation, hybridoma technologies, polymerase chain reaction (PCR), vector and expression technologies, host cell culture, and protein purification methods. In the following, the terms "antibody" and "antibody molecule" are used interchangeably.

"Specific for CD44" shall mean that the antibody molecule has specific binding affinity for, i.e., specifically binds an epitope present in CD44. In a preferred embodiment, the antibody molecule of the invention has a binding specificity for the amino acid sequence coded by variant exon v6 of the human CD44 gene. The sequence of variant exon v6 as well as of the other variant exons is known in the art (Screaton G. R., et al., Proc. Natl. Acad. Sci. USA 89:12160-12164, 1992; Tölg C. et al. Nucleic Acids. Res. 21:1225-1229, 1993; Hofmann, M. et al. Cancer Res. 51:5292-5297, 1991). A preferred antibody molecule of the invention specifically binds to peptides or polypetides having or containing the amino acid sequence SEQ ID NO:1 of the accompanying sequence listing, or an allelic variant of said sequence. A preferred antibody molecule of the invention specifically binds to peptides or polypeptides consisting of or comprising the amino acid sequence SEQ ID NO:1, or an allellic variant thereof. Preferably, said antibody molecule has binding specificity for an epitope contained within said sequence, i.e., specifically binds said sequence. More preferably, the antibody molecule specifically binds to a peptide having the amino acid sequence SEQ ID NO:2, even more preferably having the amino acid sequence SEQ ID NO:3. Such antibody molecules may be easily produced with methods known in the art (WO 95/33771, WO 97/21104), e.g. by immunising laboratory animals with chemically synthesised peptides having the aforementioned sequences, e.g., bound to a hapten, or immunising with a recombinantly produced fusion protein including said sequences, and proceeding according to methods known in the art (Harlow LD. Cold Spring Harbor Lab. 1988; Catty D. Oxford IR Press, 1988; Koopman G. et al. Exp. Med. 177:897-904, 1993).

Preferably, an antibody molecule according to the invention is the murine monoclonal antibody with the designation VFF-18 which is produced by a hybridoma cell line which has been deposited on 7 Jun. 1994 under the accession number DSM ACC2174 with the DSM-Deutsche Sammlung für Mikroorganismen und Zellkulturen GmbH, Mascheroder Weg 1b, D-38124 Braunschweig, Deutschland/Germany under the provisions of the Budapest Treaty on the International Recognition of the Deposit of Microorganisms for the Purposes of Patent Procedures. Also preferred are Fab, Fab', or F(ab)$_2$ fragments of said monoclonal antibody VFF-18. In another preferred embodiment, the antibody molecule is a humanised recombinant antibody, wherein the complementarity determining regions (CDR's) of VFF-18 have been grafted into the respective genes of human immunoglobulin heavy and light chains.

"Complementarity determining regions" of a monoclonal antibody are understood to be those amino acid sequences involved in specific antigen binding according to Kabat E. A. et al., National Institutes of Health, Bethesda, Md. 1991, in connection with Chothia and Lesk, J. Mol. Biol. 196:901-917, 1987.

In another preferred embodiment, appropriate framework residues of such a CDR-grafted antibody are reverted to murine residues to improve binding affinity. From methods pertinent to the art, one skilled in the art knows how to obtain the CDR's of VFF-18, starting with the aforementioned hybridoma with the accession number DSM ACC2174, to choose and obtain appropriate human immunoglobulin genes, to graft the CDR's into these genes, to modify selected framework residues, to express the CDR-grafted antibody in appropriate host cells, e.g. Chinese hamster ovary (CHO) cells, and to test the resulting recombinant antibodies for binding affinity and specificity (see e.g. literature references above). In another preferred embodiment of the invention, the antibody molecule is a recombinant antibody having the CDR's of the antibody VFF-18. Preferably, such a recombinant antibody is a humanised antibody and is a complete immunoglobulin consisting of two complete light and two complete heavy chains. In another preferred embodiment of the invention, the antibody molecule is a recombinant antibody having the same idiotype as the antibody VFF-18. In another preferred embodiment of the invention, the antibody molecule is a recombinant antibody binding to the same epitope as the antibody VFF-18.

In a particular preferred embodiment, the antibody molecule A is an antibody comprising light chains having the amino acid sequence SEQ ID NO:4, and heavy chains having the amino acid sequence SEQ ID NO:6. This antibody is called BIWA 4. It is a humanised version of antibody VFF-18 mentioned above, having the complementary determining regions of the murine monoclonal antibody VFF-18 in a completely human framework, and human constant regions. It is therefore an antibody of very low immunogenicity in man, which is a favorable trait. However, as it has no murine framework residues to optimise antigen binding, it has a significanty lower antigen binding affinity than its parent antibody VFF-18, and therefore would not have been regarded as a good candidate for a therapeutic drug. Unexpectedly, it has been found that BIWA 4, despite its poor binding affinity, has a very favorable biodistribution and tumor uptake in vivo, making it superior to other humanised versions of VFF-18 with higher binding affinity. In a further preferred embodiment, the antibody molecule A is an antibody comprising light chains having the amino acid sequence SEQ ID NO:8, and heavy chains having amino acid sequence SEQ ID NO:6. This antibody has higher binding affinity than BIWA 4.

These antibodies may be produced as follows. Nucleic acid molecules coding for the light chain and the heavy chain may be synthesised chemically and enzymatically by standard methods. First, suitable oligonucleotides can be synthesized with methods known in the art (e.g. Gait M. J., IRL Press, Oxford, UK, 1984), which can be used to produce a synthetic gene. Methods to generate synthetic genes from oligonucleotides are known in the art (e.g. Stemmer et al. Gene 164(1):49-53, 1995; Ye et al. Biochem Biophys Res Commun 186(1):143-9, 1992; Hayden and Mandecki DNA 7(8):571-7, 1988; Frank et al. Methods Enzymol 154:221-249, 1987). Preferably, the nucleic acid molecules encoding the light and heavy chains of BIWA 4 have the nucleotide sequences of SEQ ID NO:5 and SEQ ID NO:7, respectively. These sequences include sequences coding for leader peptides which are cleaved by the host cell (SEQ ID NO:5: the first 60 nucleotides; SEQ ID NO:7: the first 57 nucleotides). In a further embodiment, the nucleic acid molecules encoding the light and heavy chains of an antibody molecule according to the invention have the nucleotide sequences of SEQ ID NO:9 and SEQ ID NO:7, respectively. These nucleic acid molecules encoding the antibody heavy and light chains then may be cloned into an expression vector (either both chains in one vector molecule, or each chain into a separate vector molecule), which then is introduced into a host cell. Expresssion vectors suitable for immunoglobulin expression in prokaryotic or eukaryotic host cells and methods of introduction of vectors into host cells are well-known in the art. In general, the immunoglobulin gene therein is in functional connection with a suitable promoter, like for example a human cytomegalovirus (CMV) promoter, hamster ubiquitin promoter (WO 97/15664), or a simian virus SV40 promoter located upstream of the Ig gene. For termination of transcription, a suitable termination/polyadenylation site like that of the bovine growth hormone or SV40 may be employed. Furthermore, an enhancer sequence may be included, like the CMV or SV40 enhancer. Usually, the expression vector furthermore contains selection marker genes like the dihydrofolate reductase (DHFR), glutamine synthetase, adenosine deaminase, adenylate deaminase genes, or the neomycin, bleomycin, or puromycin resistance genes. A variety of expression vectors are commercially available from companies such as Stratagene, La Jolla, Calif.; Invitrogen, Carlsbad, Calif.; Promega, Madison, Wis. or BD Biosciences Clontech, Palo Alto, Calif. For example, expression vectors pAD-CMV1 (NCBI GenBank Accession No. A32111) or pAD-CMV19 (NCBI GenBank Accession No. A32110) may be used for expression. The host cell preferably is a mamalian host cell, e.g. a COS, CHO, or BHK cell, more preferably a chinese hamster ovary (CHO) cell, e.g. a CHO-DUKX (Urlaub and Chasin, Proc. Natl. Acad. Sci. USA 77(7):4216-20, 1980), CHO-DG44 (Urlaub et al., Cell 33:405-412, 1983), or CHO-K1 (ATCC CCL-61) cell. The host cell then is cultured in a suitable culture medium under conditions where the antibody is produced, and the antibody is then isolated from the culture according to standard procedures. Procedures for production of antibodies from recombinant DNA in host cells and respective expression vectors are well-known in the art (see e.g. WO 94/11523, WO 97/9351, EP 0 481 790, EP 0 669 986).

In order to link the antibody molecule A to the compound B which is toxic to cells, a linking moiety L is used. In the most simple case, the linking moiety L is a chemical bond, preferably a covalent bond which is cleaved under intracellular conditions, for example, by intracellular esterases. In one embodiment of the invention, the bond is between a sulfur atom present in the antibody molecule, e.g. in the side chain of a cystein residue, and another sulfur atom present in the toxic compound. In another embodiment, the linking moiety L consists of one or more atoms or chemical groups. Suitable linking groups are well known in the art and include disulfide groups, thioether groups, acid labile groups, photolabile groups, peptidase labile groups and esterase labile groups. Preferred are disulfide groups and thioether groups.

Conjugates of the antibody molecules of the invention and toxic compound can be formed using any techniques presently known or later developed. The toxic compound can be modified to yield a free amino group and then linked to the antibody molecule via an acid-labile linker, or a photolabile linker. The toxic compound can be condensed with a peptide and subsequently linked to an antibody molecule to produce a peptidase-labile linker. The toxic compound can be treated to yield a primary hydroxyl group, which can be succinylated and linked to an antibody molecule to produce a conjugate that can be cleaved by intracellular esterases to liberate free drug. Most preferably, the toxic compound is treated to create a free or protected thiol group, and then one or many disulfide or thiol-containing toxic compounds are covalently linked to the antibody molecule via disulfide bond(s).

For example, antibody molecules can be modified with crosslinking reagents such as N-succinimidyl 3-(2-pyridyldithio)propionate (SPDP), 4-succinimidyl-oxycarbonyl-α-methyl-α-(2-pyridyldithio)-toluene (SMPT), N-succinimidyl-3-(2-pyridyldithio)-butyrate (SDPB), N-succinimidyl-4-(2-pyridyldithio)pentanoate (SPP), N-succinimidyl-5-(2-pyridyldithio)pentanoate, 2-iminothiolane, or acetylsuccinic anhydride by known methods. See, Carlsson et al, Biochem. J. 173:723-737, 1978; Blattler, et al. Biochem. 24:1516-1524, 1985; Lambert et al. Biochem. 22:3913-3920, 1983; Klotz et al, Arch. Biochem. Biophys. 96:605, 1962; Liu et al, Biochem. 18:690, 1979; Blakey and Thorpe, Immunoconjugates and Radiopharmaceuticals 1:1-16, 1988; Worrell et al. Anti-Cancer Drug Design 1:179-184, 1986. In a preferred embodiment, the linker moiety is a 4-thiopentanoate derived from SPP. The antibody molecule containing free or protected thiol groups thus derived is then reacted with a disulfide- or thiol-containing toxic compound to produce conjugates. The conjugates can be purified by HPLC or by gel filtration.

"Toxic compound" is a compound that inhibits or prevents function of cells and/or causes cell destruction. Toxic compounds used for coupling may be either cytostatic or cytotoxic and lead to cell cycle arrest or cell death. These compounds may act at different stages during the cell cycle, e.g. by interference with nucleic acid synthesis, inactivation of nucleic acids, or by binding to tubulin.

In a preferred embodiment, the compound B which is toxic to cells is a maytansinoid, i.e. a derivative of maytansine (CAS 35846538). In a preferred embodiment, it is a C-3 ester of maytansinol. Maytansinoids suitable for conjugating to antibodies for use in cancer therapy, including preparation of said maytansinoids and their linkage to antibody molecules, have been described by Chari and coworkers (Chari R V J, et al. Cancer Research 52:127-31, 1992; Liu C. et al., Proc Natl Acad Sci USA 93:8618-23, 1996; U.S. Pat. No. 5,208,020). These maytansinoids may be used for the present invention. In a preferred embodiment, the toxic compound is $N^{2'}$-deacetyl-$N^{2'}$-(3-mercapto-1-oxopropyl)-Maytansine (CAS Number 139504-50-0), also referred to as DM1. Preferably, said maytansinoid is a maytansinol derivative linked to the antibody molecule via a disulfide bridge at the C-3 position of maytansinol. In a particularly preferred embodiment, the antibody/maytansinoid conjugate may be prepared from a maytansinoid of formula:

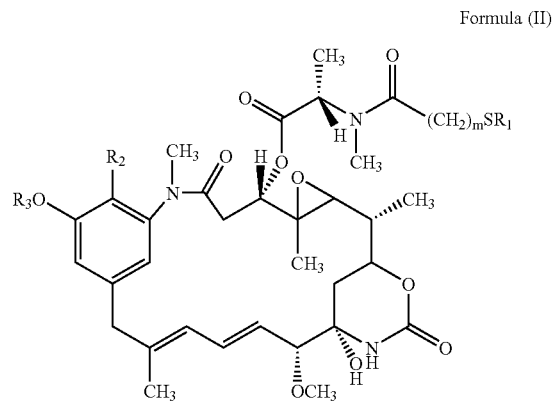

Formula (II)

wherein $R_1$ represents H or $SR_4$, wherein $R_4$ represents methyl, ethyl, linear alkyl, branched alkyl, cyclic alkyl, simple or substituted aryl, or heterocyclic;

$R_2$ represents Cl or H;

$R_3$ represents H or $CH_3$; and m represents 1, 2, or 3.

Preferably, $R_1$ is H, $CH_3$, or $SCH_3$, $R_2$ is Cl, $R_3$ is $CH_3$, and m=2.

The compound with $R_1$=H, $R_2$=Cl, $R_3$=$CH_3$, and m=2 is designated DM1 in the literature.

In a preferred embodiment, the compound of the invention has the formula:

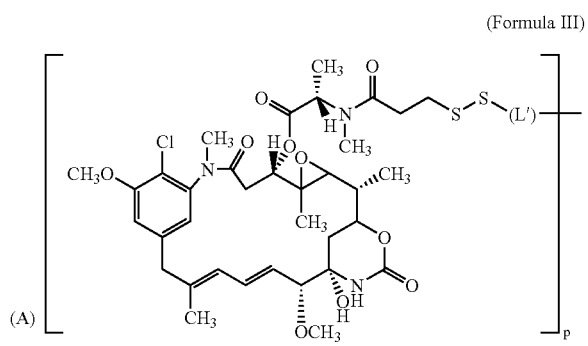

(Formula III)

wherein

A is an antibody molecule which is specific for CD44, preferably specific for the variant exon v6, preferably specific for the amino acid sequence SEQ ID NO:3;

(L') is an optional linker moiety p is a decimal number with p=1 to 10.

Preferably, p is 3 to 4, more preferably about 3.5.

Methods for preparing such maytansinoids are known in the art (see in particular U.S. Pat. No. 5,208,020, Example 1). Conveniently, in a first step the maytansinoid C-3 ester ansamitocin P3 may be produced by bacterial fermentation (U.S. Pat. Nos. 4,356,265; 4,450,234; WO 01/77360) of microorganisms belonging to the genus *Nocardia* or *Actinosynnema*, e.g. ATCC 31565, ATCC 31281. Ansamitocin P3 may be extracted from the culture using organic solvents like ethyl acetate or toluene, and further purified by adsorption chromatography using e.g. silica gel. It may then be reduced to maytansinol using LiAlH$_4$ (U.S. Pat. No. 4,360, 462) or, as suggested more recently (WO 02/16368), LiAl (OMe)$_3$H or other LiAl or NaAl hydrids. The maytansinol may then be esterified at the C-3 position with N-methyl-L-alanine or N-methyl-L-cysteine derivatives to yield a disulfide-containing maytansinoid (U.S. Pat. Nos. 5,208, 020; 5,416,064; 6,333,410), for example using dicyclohexylcarbodiimide (DCC) and catalytic amounts of zinc chloride (U.S. Pat. Nos. 4,137,230; 4,260,609). In a preferred embodiment, the maytansinol is esterified with the compound N-methyl-N-(3-methyldithiopropanoyl)-L-alanine of formula:

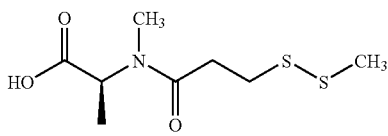

to yield the maytansinoid of Formula (II) with with R$_1$=SR$_4$, R$_4$=CH$_3$, R$_2$=Cl, R$_3$=CH$_3$, and m=2.

The free thiol group may then be released by cleavage of the disulfide bond with dithiothreitol (DTT) to yield, e.g., DM1.

Upon intracellular cleavage, the free toxic compound is released. The free drug released from the compound A(LB)$_n$ may have the formula B-X, wherein X is an atom or a chemical group, depending on the nature of the cleaving reaction. Preferably, X is a hydrogen atom, as for example when the linker moiety is just a covalent bond between two sulfur atoms, or a hydroxyl group. The cleavage site may also be within the linker moiety if the linker moiety is a chemical group, generating free drug of formula B-L"-X upon cleavage, wherein X is an atom or a chemical group, depending on the nature of the cleaving reaction. Preferably, X is a hydrogen atom or a hydroxyl group.

In a preferred embodiment, the compound of formula (I) is less toxic than the toxic compound B, B-X or B-L"-X released upon intracellular cleavage. Methods of testing cytotoxicity in vitro are known in the art (Goldmacher et al. J. Immunol. 135:3648-3651, 1985; Goldmacher et al. J. Cell Biol. 102:1312-1319, 1986; see also U.S. Pat. No. 5,208, 020, Example 2). Preferably, the compound (I) is 10 times or more, more preferably 100 times or more, or even 1000 times or more less toxic than the free drug released upon cleavage.

Preferably, antibody molecule/maytansinoid conjugates are those that are joined via a disulfide bond, as discussed above, that are capable of delivering maytansinoid molecules. Such cell binding conjugates are prepared by known methods such as modifying monoclonal antibodies with succinimidyl pyridyl-dithiopropionate (SPDP) or pentanoate (SPP) (Carlsson et al. Biochem J. 173:723-737, 1978). The resulting thiopyridyl group is then displaced by treatment with thiol-containing maytansinoids to produce disulfide linked conjugates. Alternatively, in the case of the aryldithiomaytansinoids, the formation of the antibody conjugate is effected by direct displacement of the aryl-thiol of the maytansinoid by sulfhydryl groups previously introduced into antibody molecules. Conjugates containing 1 to 10 maytansinoid drugs linked via a disulfide bridge are readily prepared by either method. In this context, it is understood that the decimal number n in the formula A(LB)$_n$ is an average number as not all conjugate molecules of a given preparation may have the identical integer of LB residues attached to the antibody molecule.

More specifically, a solution of the dithiopyridyl modified antibody at a concentration of 1 mg/ml in 0.1M potassium phosphate buffer, at pH 7.0 containing 1 mM EDTA is treated with the thiol-containing maytansinoid (1.25 molar equivalent/dithiopyridyl group). The release of pyridine-2-thione from the modified antibody is monitored spectrophotometrically at 343 nm and is complete in about 30 min. The antibody-maytansinoid conjugate is purified and freed of unreacted drug and other low molecular weight material by gel filtration through a column of Sephadex G-25. The number of maytansinoids bound per antibody molecule can be determined by measuring the ratio of the absorbance at 252 nm and 280 nm. An average of 1-10 maytansinoid molecules/antibody molecule can be linked via disulfide bonds by this method.

In a further aspect, the present invention relates to a conjugate of a CD44v6 specific antibody molecule and a maytansinoid. Herein, "CD44v6 specific" shall mean that the antibody has specific binding affinity to an epitope which is present in a peptide having the amino acid sequence encoded by variant exon v6 of CD44, preferably human CD44. A preferred antibody molecule of the invention specifically binds to peptides or polypetides having or containing the amino acid sequence SEQ ID NO:1 of the accompanying sequence listing, or an allelic variant of said sequence. Preferably, said antibody molecule has binding specificity for an epitope within said sequence. More preferably, the antibody molecule specifically binds to a peptide having the amino acid sequence SEQ ID NO:2, even more preferably having the amino acid sequence SEQ ID NO:3.

Preferably, the antibody molecule in said conjugate is the monoclonal antibody VFF-18 (DSM ACC2174) or a recombinant antibody having the complementary determining regions (CDRs) of VFF-18. More preferably, the said antibody comprises light chains having the amino acid sequence SEQ ID NO:4 or, alternatively, SEQ ID NO:8, and heavy chains having the amino acid sequence SEQ ID NO:6.

The maytansinoid is preferably linked to the antibody by a disulfide moiety and has the formula:

Formula (IV)

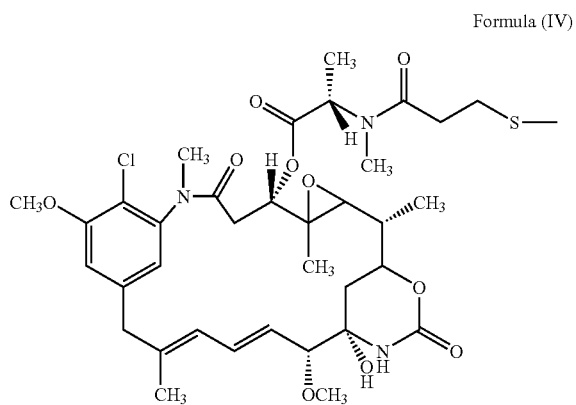

wherein the link to the antibody is through the sulfur atom shown in formula IV to a second sulfur atom present in the antibody molecule. To create such a sulfur atom available for bonding, an antibody molecule may be modified by introduction of a suitable linker as outlined above. Preferably, the maytansinoid is linked to the antibody molecule through a —S—CH$_2$CH$_2$—CO—, a —S—CH$_2$CH$_2$CH$_2$CH$_2$—CO—, or a —S—CH(CH$_3$)CH$_2$CH$_2$—CO—group. The sulfur atom in such a linker group forms the disulfide bond with the maytansinoid, while the carbonyl function may be bonded to an amino function present on the side chain of an amino acid residue of the antibody molecule.

That way, one or more maytansinoid residues may be linked to an antibody molecule. Preferably, 3 to 4 maytansinoid residues are linked to an antibody molecule. Most preferred is a conjugate of a CD44v6 specific antibody molecule and a maytansinoid, wherein the antibody comprises light chains having the amino acid sequence SEQ ID NO:4, and heavy chains having the amino acid sequence SEQ ID NO:6, and wherein the maytansinoid has the formula:

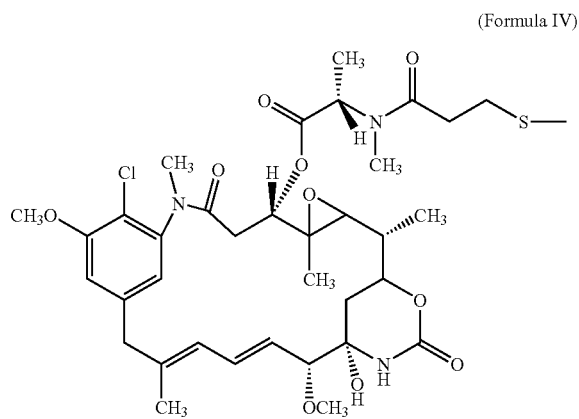

(Formula IV)

and is linked to the antibody through a disulfide bond. Preferably, the linking group is —S—CH$_2$CH$_2$CH$_2$CH$_2$—CO— or —S—CH(CH$_3$)CH$_2$CH$_2$—CO—, and the number of maytansinoid residues bound per antibody molecule is 3 to 4.

In a further embodiment, the present invention relates to a method of production of a compound of formula (I) comprising the steps:
 (a) introducing free or protected thiol groups into an antibody molecule which is specific for CD44;
 (b) reacting the antibody molecule of step (a) with a compound which is toxic to cells, said compound having one or more disulfide or thiol groups; and
 (c) recovering the resulting conjugate.

Preferably, the antibody molecule is specific for CD44v6, more preferably specific for the amino acid sequence SEQ ID NO:3. The compound which is toxic to cells is preferably a maytansinoid, more preferably of formula (II), most preferably with R$_1$=H, R$_2$=Cl, R$_3$=CH$_3$, and m=2. In a further preferred embodiment, the antibody comprises light chains having the amino acid sequence SEQ ID NO:4 or SEQ ID NO:8, and heavy chains having the amino acid sequence SEQ ID NO:6.

In preferred embodiments, (2-pyridyl)-3-dithiopropanoic acid N-hydroxy succinimid ester (N-succinimidyl-3-(2-pyridyldithio)-propionate), (2-pyridyl)-4-dithiopentanoic acid N-hydroxy succinimid ester (N-succinimidyl-4-(2-pyridyldithio)-pentanoate), or (2-pyridyl)-5-dithiopentanoic acid N-hydroxy succinimid ester (N-succinimidyl-5-(2-pyridyldithio)-pentanoate) are used to introduce the free or protected thiol groups into the antibody molecule. The invention also relates to compounds obtainable by a method as described.

In a further embodiment, the present invention relates to a pharmaceutical composition comprising a compound of formula (I), or a conjugate as described, preferably together with a pharmaceutically acceptable carrier, excipient, or diluent.

Suitable pharmaceutically acceptable carriers, diluents, and excipients are well known and can be determined by those of skill in the art as the clinical situation warrants. Examples of suitable carriers, diluents and/or excipients include but are not limited to: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

More preferably, the antibody molecule present in the pharmaceutical composition is the monoclonal antibody VFF-18, or a recombinant antibody having the CDR's of the antibody VFF-18, preferably in a human framework. In a further preferred embodiment, the antibody comprises light chains having the amino acid sequence SEQ ID NO:4 or SEQ ID NO:8, and heavy chains having the amino acid sequence SEQ ID NO:6. Preferably, the toxic compound is the maytansinoid of formula (II).

The conjugate may, for example, be clinically used ex vivo to remove tumor cells from bone marrow prior to autologous transplantation in cancer treatment. Treatment can be carried out as follows. Bone marrow is harvested from the patient or other individual and then incubated in medium containing serum to which is added the compound of formula (I) according to the invention, concentrations range from about 10 μM to 1 pM, for about 30 minutes to about 48 hours at about 37° C. The exact conditions of concentration and time of incubation (=dose) are readily determined by the skilled artisan. After incubation, the bone marrow cells are washed with medium containing serum and returned to the patient by i.v. infusion according to known methods. In circumstances where the patient receives other treatment such as a course of ablative chemotherapy or total-body irradiation, between the time of harvest of the marrow and reinfusion of the treated cells, the treated marrow cells are stored frozen in liquid nitrogen using standard medical equipment.

In a further embodiment, the present invention relates to a method of treatment of cancer comprising applying a pharmaceutical composition as described before to a patient. In particular, this aspect of the invention relates to a method of treatment of cancer in a patient in need thereof comprising administering to the patient a therapeutically effective amount of a compound as described above, or a pharmaceutical composition as described above. Preferably, the cancer is head and neck squamous cell carcinoma (SCC), esophagus SCC, lung SCC, skin SCC, breast adenocarcinoma (AC), lung AC, cervix SCC, pancreas AC, colon AC, or stomach AC.

For clinical treatment of cancer, the compound of formula (I) according to the invention will be supplied as solutions that have been tested for sterility and for endotoxin levels. Examples of suitable protocols of conjugate administration are as follows. Conjugates may be given weekly for 1 to 6 weeks either as an i.v. bolus, or as a continuous infusion for 5 days. Bolus doses can be given in 50 to 100 ml of normal saline to which 5 to 10 ml of human serum albumin has been added. Continuous infusions can be given in 250 to 500 ml of normal saline, to which 25 to 50 ml of human serum albumin has been added, per 24 hour period. Dosages will be 10 mg to 400 mg/m² of body surface area per application. The dose applied to the patient per administration has to be high enough to be effective, but must be below the dose limiting toxicity (DLT). In general, a sufficiently well tolerated dose below DLT will be considered maximum tolerated dose (MTD). The expert knows how to determine the MTD (Lambert J M et al. American Association of Cancer Research 39:Abs 3550, 1998). For weekly administrations, the MTD can be expected to be in the range of 100 to 200 mg/m². Alternatively, intervals between applications may be longer, e.g. two to four weeks, preferably three weeks. In this case, the MTD can be expected to be in the range of 200 to 300 mg/m². Alternatively, application may be in 5 daily doses, followed by a break of several weeks after which treatment may be repeated. In this case, the MTD per administration can be expected to be lower than 100 mg/m². For example, conjugates can be administered as a single i.v. infusion with a rate of 3 mg/min every 21 days. Up to 7 cycles of treatment were applied.

Dose, route of administration, application scheme, repetition and duration of treatment will in general depend on the nature of the disease (type, grade, and stage of the tumor etc.) and the patient (constitution, age, gender etc.), and will be determined by the medical expert responsible for the treatment. Besides treatment of solid tumors, therapeutic application according to the invention may be particularly advantageous as an adjuvant to surgical intervention, to treat minimal residual disease.

In a further embodiment, the invention relates to the use of a compound of formula (I) for the preparation of a pharmaceutical composition for the treatment of cancer. More preferably, the antibody molecule present in the pharmaceutical composition is the monoclonal antibody VFF-18, or a recombinant antibody having the CDR's of the antibody VFF-18, preferably in a human framework. Most preferred is an antibody molecule comprising a light chain having SEQ ID NO:4 or SEQ ID NO:8, and a heavy chain having SEQ ID NO:6. Preferably, the toxic compound has the formula (II). Preferably, the cancer is head and neck squamous cell carcinoma (SCC), esophagus SCC, lung SCC, skin SCC, breast adenocarcinoma (AC), lung AC, cervix SCC, pancreas AC, colon AC, or stomach AC.

EXAMPLES

1. Material and Methods 1.1. In Vitro Cell Proliferation Assay

For determination of viable cells the Cell Titer 96® AQ$_{ueous}$ non-radioactive cell proliferation assay (Promega, Wisconsin, Wis.) was used. Five thousand cells per well were seeded into 96-well plates in 90 μl medium without phenol red. Cells were allowed to settle for 1 to 3 h and then serial dilutions of the immunoconjugate in 10 μl PBS were added. Cells without immunoconjugate served as negative control. Cells were incubated for 4 days at 37° C. in a humified 5% $CO_2$ atmosphere and then 20 μl MTS/PMS (3-(4,5-dimethylthiazol-2-yl)-5-(3-carboxymethoxyphenyl)-2-(4-sulfophenyl)-2H-tetrazolium/phenazine formazan) were added according to the manufacturer's recommendation. After an additional 1 to 4 h incubation at 37° C., the absorbance at 490 nm was recorded using an ELISA plate reader. For each cell line, triplicates were analyzed. The percentage of the surviving cell fraction and the $IC_{50}$ value were calculated using the GraphPad Prism® (Version 3.0) software.

1.2. Manufacturing of BIWI 1

Humanised recombinant antibodies BIWA 4 and BIWA 8 which have binding specificity for an epitope within SEQ ID NO:1 were linked to the maytansinoid DM1 as described below. The conjugate of BIWA 4 with DM1 was designated BIWI 1.

Generation of stably transfected cell lines. The genes coding for the light and heavy chains of BIWA 4, SEQ ID NO:5 and SEQ ID NO:7, were ligated into expression vector pAD-CMV1 (WO92/01055; NCBI GenBank Accession No. A32111) or pAD-CMV19 (NCBI GenBank Accession No. A32110). For the second antibody BIWA 8, the light chain was coded by a gene having SEQ ID NO:9, while the heavy chain was the same as in BIWA 4. Stably transfected cell lines were generated by electroporation as follows. CHO DUX/57ss (dhfr negative mutant of Chinese Hamster Ovary cells, adapted for serum free suspension culture) were used. After trypsinization and inactivation of trypsin with RPMI-10 (90% RPMI 1640, 10% heat inactivated fetal calf serum), cells were washed once with RPMI-0 (RPMI 1640 without serum), and 1×10⁷ cells were resuspended in 0.8 ml RPMI-0. After addition of the linearised DNA (20 μg per plasmid; cotransfection of vectors coding for light and heavy chain), the cells were electroporated using a Hoefer Electroporator under the following conditions: 1080 μF, 320 V, 1000 msec, 1 pulse. Cells were allowed to stand for 5 min, and were then diluted to 12500 cells/ml and 2500 cells/ml in alpha-MEM 10d (90% MEM alpha without ribonucleosides and without deoxyribonucleosides (GIBCO BRL), 10% heat inactivated dialysed fetal calf serum). The cells were seeded into 96 well microtiter plates (200 μl/well, corresponding to 2500 and 500 cells/well respectively). Clones appeared after 10 days. Only the plates with 500 cells/well were followed up (3-6 clones/well). After 14-15 days, supernatants from each well were tested in a κ/γ ELISA. 53 clones were seeded in 12 well plates in alpha-MEM 10d. After 3-6 days (depending on the confluency of the cells) supernatants were tested again in the κ/γ ELISA (serial dilutions) and quantitated using a human IgG1 standard. Cells were frozen and stored in liquid nitrogen. IgG contents of the 53 clones ranged from 12-417 ng/ml. Ten clones with the highest expression level were selected and subcloned as follows: Cells of each clone were seeded into 96 well microtiter plates with densities of 1 and 5 cells/well in 100 μl/well alpha-MEM 10d (1 plate for each clone and each density). Eight days later supernatants were diluted 1:2 and 100 μl of this dilution tested in the κ/γ ELISA and quantitated using a BIWA 4 preparation as standard. Five subclones of each clone were transferred to 12 well plates. The IgG content ranged from 1.3-908 ng/ml. Fourteen clones with the highest expression level (384-908 ng/ml) were used for amplification with methotrexate as follows: Clones were initially cultured in 25 cm² flasks containing alpha-MEM 10d with 20, 50 and 100 nM methotrexate. After the outgrowth of clones the supernatants were tested in the κ/γ ELISA. In subsequent rounds of amplification the methotrexate concentration was raised up to 2000 nM. Initially the highest expression level ranged from 10.5-14.8 μg/ml (clone A31/100, 100 nM methotrexate). Further amplification with a methotrexate concentration of 500 nM gave an expression of 19-20 μg/ml (A31/500).

Purification of antibody. Antibody was purified from cell culture supernatant as follows. Antibody containing tissue culture supernatant was applied onto a 5 ml protein A sepharose column with a flow rate of 80-90 ml/h at 4° C. After washing with 50 ml binding buffer (0.1 M sodium phosphate pH 7.5), the Ig fraction was eluted with elution buffer (0.1 M glycine-HCl pH 2.7). Absorption at 280 nm was monitored.

Modification of BIWA 4 with SPP to form BIWA 4-SS-Py. BIWA 4 was supplied in liquid form at a concentration of 5 mg/mL in a PBS formulation containing Tween 20. Prior to coupling of DM1 to the MAb (monoclonal antibody) the Tween 20 was removed. The MAb solution (40 mL) was diluted 15-fold with 25 mM MES buffer, pH 5.6, containing 50 mM NaCl (MES buffer) and then loaded onto a column (12.5 mL) of Sepharose S equilibrated in MES buffer (flow rate: 100 cm/hr). The column was washed with 10 column volumes of MES buffer. The antibody was eluted with MES buffer containing 400 mM NaCl. The antibody solution was dialysed against 50 mM potassium phosphate buffer, pH 6.5 containing 50 mM NaCl and 2 mM EDTA (Buffer A). The BIWA 4 antibody was modified using SPP ((2-Pyridyl)-5-dithiopentanoic acid N-hydroxy succinimid ester) to introduce dithiopyridyl groups. The MAb in Buffer A (185 mg, 8 mg/mL) was modified with a 7-fold molar excess of SPP in EtOH (5% v/v of MAb solution). The reaction proceeded for 90 minutes at ambient temperature. The reaction mixture was then subjected to gel filtration chromatography through Sephadex G25F (2.6×31.5 cm column, 167 mL) equilibrated in Buffer A. MAb-containing fractions were pooled and the degree of modification was determined by measuring the absorbance at 280 nm and the change in absorbance at 343 nm caused by the release of 2-mercaptopyridine by the addition of DTT. The concentration of released 2-mercaptopyridine was calculated using an $\epsilon_{343\ nm}$ of 8080 $M^{-1}$ $cm^{-1}$, and the concentration of MAb was calculated using an $\epsilon_{280\ nm}$ of 224,000 $M^{-1}$ $cm^{-1}$ after the absorbance at 280 nm had been corrected for the contribution from 2-mercaptopyridine. (2-mercaptopyridine $A_{280\ nm}=A_{343\ nm}\times5100/8080$). Recovery of the MAb was 99.6% with 5.5 releasable 2-mercaptopyridine groups linked per MAb molecule.

Conjugation of BIWA 4-SS-Py with DM1. The above modified MAb (184 mg) in Buffer A was conjugated at 2.5 mg MAb/mL using a 1.7-fold molar excess of DM1 over releasable 2-mercaptopyridine groups. DM1 was added in DMA (3% v/v of MAb solution) and the reaction mixture was incubated at ambient temperature for 29 hours. The conjugate was then isolated by gel filtration chromatography on a column of Sephacryl S300 HR equilibrated in PBS (5×50 cm column, 980 mL, flow rate of 10 cm/hr). The conjugate eluted as a single peak at the position of monomeric MAb with a small amount of protein eluting earlier. Fractions were assayed for the number of DM1 molecules linked per MAb molecule. (Linked DM1 molecules were determined by measuring the absorbance at both 252 nm and 280 nm). Based on the results, fractions representing 63-77% of the column volume were pooled. The DM1/MAb ratio in the pooled solution was found to be 3.1 and the yield of conjugated BIWA 4 was 75% based on starting MAb. The conjugate, BIWI 1, was evaluated by SDS-PAGE performed under non-reducing conditions and found to be composed primarily of a monomer species (>95%) with a minor amount (<5%) of dimeric conjugate.

Analysis of in vitro binding of BIWI 1. The binding of BIWA 4 antibody and BIWI 1 conjugate to antigen-positive FaDu cells (human head and neck cancer cell line) was determined. Cells ($1-2\times10^{-5}$) were incubated in 96-well plates with varying concentrations of antibody or conjugate on ice for 1 hour. The test substance was washed from the plate and FITC-labeled anti-human IgG was added and the incubation on ice was continued in the dark for 1 hour. After washing, the cells were fixed with 1% paraformaldehyde and analyzed on a fluorescence activated cell sorter (FACS). BIWA 4 antibody bound with an apparent $K_D$ of $1\times10^{-9}$ M and BIWI 1 bound with an apparent $K_D$ of $1.8\times10^{-9}$ M. Thus, conjugation with DM1 alters the binding affinity of the antibody only slightly if at all.

1.3. Efficacy Studies in Nude Mice

In vivo anti-tumor efficacy of BIWI 1 was tested in two nude mouse xenograft models applying antigen-positive human tumors, which differed in tumor origin, extent and homogeneity of CD44v6 expression: A431 (ATCC # CRL 1555; epidermoid carcinoma of the vulva), FaDu (ATCC # HTB 43; squamous cell carcinoma of the pharynx). Tumor cell lines A431 and FaDu were received from ATCC and cultured in RPMI1640 medium containing 10% fetal calf serum and supplements.

Mice were randomised into the following treatment groups (treatment/initial mean tumour volume/tumour volume range/number of mice):

A431

| | |
|---|---|
| Group 1: | Control (PBS)/185 ± 217 mm³/19-424 mm³/5 mice. |
| Group 2: | BIWA 4 (21 mg/kg/d)/133 ± 115 mm³/42-302 mm³/5 mice. |
| Group 3: | BIWI 1 (2.1 mg/kg/d)/107 ± 63 mm³/42-205 mm³/5 mice. |
| Group 4: | BIWI 1 (7 mg/kg/d)/132 ± 73 mm³/42-205 mm³/5 mice. |
| Group 5: | BIWI 1 (21 mg/kg/d)/107 ± 63 mm³/42-205 mm³/5 mice. |

FaDu

| | |
|---|---|
| Group 1: | Control (PBS)/142 ± 82 mm³/34-268 mm³/8 mice. |
| Group 2: | BIWA 4 (21 mg/kg/d)/134 ± 86 mm³/42-268 mm³/6 mice. |
| Group 3: | BIWI 1 (2.1 mg/kg/d)/149 ± 96 mm³/50-268 mm³/6 mice. |
| Group 4: | BIWI 1 (7 mg/kg/d)/132 ± 97 mm³/42-268 mm³/6 mice. |
| Group 5: | BIWI 1 (21 mg/kg/d)/129 ± 74 mm³/50-231 mm³/6 mice. |

$1\times10^6$ tumors cells were transplanted subcutaneously into the right flank of 6 week old female NMRI-nu/nu mice. Treatment started when the tumors reached an average size of 102 to 185 mm³. Treatment consisted of i.v. injections of BIWI 1 given on five consecutive days, starting at day 1. Three different doses of BIWI 1 were tested in parallel: 2.1 mg/kg/d BIWI 1 corresponding to 30 µg/kg/d DM1, 7 mg/kg/d BIWI 1 corresponding to 100 µg/kg/d DM1, and 21 mg/kg/d BIWI 1 corresponding to 300 µg/kg/d DM1. Control animals were either untreated (PBS) or treated with unconjugated antibody (control antibody, 21 mg/kg/d). Tumor growth was monitored by measuring tumor size. A tumor response was rated as complete response when the tumor completely disappeared at any time after start of treatment. The response was rated as partial response when the tumor volume decreased after treatment but thereafter started regrowing. The tolerability of the treatment was monitored by measuring mouse weight during the whole observation period.

2. Results and Discussion 2.1. In vitro Cytotoxicity of BIWI 1

The in vitro cytotoxicity of BIWI 1 was evaluated using the antigen-positive cell lines A431 and FaDu, and the antigen-negative cell line A459. Cells were exposed to different concentrations of BIWI 1 for 4 days, then stained with MTS/PMS and assayed on an ELISA plate reader. The surviving fractions of cells were then calculated using the GraphPad Prism® software package. The results are shown in FIG. 1. BIWI 1 was effective in killing the antigen-positive A431 cells with an $IC_{50}$ of about $7.6\times10^{-8}$ M and the second antigen-positive cell line, FaDu, with an $IC_{50}$ of about $2.4\times10^{-8}$ M. The antigen-negative cell line, A549, was affected by the conjugate with an $IC_{50}$ of about $1.3\times10^{-7}$ M with a surviving fraction of 50% at the highest concentration of BIWI 1 tested ($5\times10^{-7}$ M). These results show that BIWI 1 is only slightly more cytotoxic against antigen-positive cells than antigen-negative cells in vitro.

2.2. Efficacy in A431 Xenografted Nude Mice

Groups of 5 mice were treated with 2.1 mg/kg/d BIWI 1, 7 mg/kg/d BIWI 1, 21 mg/kgld BIWI 1, and 21 mg/kg/d control antibody, respectively. The average tumor size at start of treatment was 185 +/−217 mm³ (PBS), 133 +/−115 mm³ (control antibody), 107 +/−63 mm³ (21 mg/kg/d BIWI 1), 132 +/−73 mm³ (7 mg/kg/d BIWI 1), and 107 +/−63 mm³ (2.1 mg/kg/d BIWI 1), respectively. The average tumor volume of each group during the observation period is shown in FIG. 2. Tumors treated with control antibody showed similar growth as untreated tumors, the tumor volume doubling time was approximately 5 days. In animals treated either with 7 mg/kg/d BIWI 1 or 21 mg/kg/d BIWI 1 all tumors responded completely and disappeared around day 17. No tumor regrowth was observed until the end of the observation period (day 134). Tumors treated with 2.1 mg/kg/d responded completely in ⅗ cases with no tumor regrowth until day 134. The remaining 2 tumors showed a partial response but ultimately regrew. These results show that BIWI 1 induces a dose-dependent anti-tumor response in A431 xenografted nude mice, with complete and long-lasting responses from 2.1 mg/kg/d BIWI 1 to 21 mg/kg/d BIWI 1. Unconjugated control antibody showed no anti-tumor effect.

See FIG. 2.

2.2. Efficacy in FaDu Xenografted Nude Mice

Groups of 6 mice were treated with 2.1 mg/kg/d BIWI 1, 7 mg/kg/d BIWI 1, 21 mg/kg/d BIWI 1, and 21 mg/kg/d control antibody, respectively. The average tumor size at start of treatment was 142 +/−82 mm³ (PBS), 134 +/−86 mm³ (control antibody), 129 +/−74 mm³ (21 mg/kg/d BIWI 1), 132 +/−97 mm³ (7 mg/kg/d BIWI 1), and 149 +/−96 mm³ (2.1 mg/kg/d BIWI 1), respectively. The average tumor volume of each group during the observation period is shown in FIG. 3. Tumors treated with control antibody and 2.1 mg/kg/d BIWI 1 showed similar growth as untreated tumors, the tumor volume doubling time was approximately 5 days. In animals treated with 21 mg/kg/d BIWI 1 all tumors responded completely and disappeared around day 24. No tumor regrowth was observed until the end of the observation period (day 107). One out of six (1/6) tumors treated with 7 mg/kg/d BIWI 1 responded completely, 3/6 tumors showed partial responses. The remaining 2 tumors grew similarly to untreated control tumors. These results show that BIWI 1 induces a dose-dependent anti-tumor response in FaDu xenografted nude mice, with complete and long-lasting responses from 7 mg/kg/d BIWI 1 to 21 mg/kg/d BIWI 1. Unconjugated control antibody shows no anti-tumor effect.

See FIG. 3.

2.4. Tolerability in Nude Mice

The tolerability of BIWI 1 treatment was determined by monitoring mouse weight during the whole duration of the experiment in the 2 models. The maximum observed average weight loss per group was 5% in FaDu xenografted mice treated with 21 mg/kg/d BIWI 1 (FIG. 4). The weight loss started around day 3 of treatment and lasted until day 10, thereafter animals regained weight and behaved similarly to control animals. In all other dose groups weight loss was similar to vehicle control (PBS). An average weight loss of 5% or less in all treatment groups indicated good tolerability of BIWI 1 treatment at the given doses in nude mice. As BIWI 1 does not cross-react with mouse CD44v6, only antigen-independent effects such as toxicity caused by free DM1 can be monitored in this experiment.

3. In vivo Anti-Tumor Efficacy in MDA-MB 453

3.1. Material and Methods

In vivo anti-tumor efficacy of BIWI 1 was tested in a nude mouse xenograft model applying the antigen-positive human tumor MDA-MB 453 (ATCC # HTB-131; breast carcinoma). The cells were received from ATCC and cultured in RPMI1640 medium containing 10% fetal calf serum and supplements. One $\times10^6$ tumors cells were transplanted subcutaneously into the right flank of 6 week old female NMRI-nu/nu mice. For therapy experiments, tumors were maintained via passaging of tumor fragments. Treatment started when the tumors reached an average size of 188 to 246 mm³. Treatment consisted of i.v. injections of BIWI 1 given weekly for four weeks. Three different doses of BIWI 1 were tested in parallel: 6.25 mg/kg BIWI 1 corresponding to 100 μg/kg DM1, 12.5 mg/kg BIWI 1 corresponding to 200 μg/kg DM1, and 25 mg/kg BIWI 1 corresponding to 400 μg/kg DM1. PBS treated animals served as tumor growth control. Tumor growth was monitored by measuring tumor size. A tumor response was rated as complete response when the tumor completely disappeared at any time after start of treatment.

3.2. Results and Discussion

Groups of 6 mice were treated with 6.25 mg/kg BIWI 1, 12.5 mg/kg BIWI 1, and 25 mg/kg BIWI 1, respectively, once a week for four weeks. The average tumor size at start of treatment was 246 +/−79 mm³ (PBS), 216 +/−85 mm³ (6.25 mg/kg BIWI 1), 188 +/−79 mm³ (12.5 mg/kg BIWI 1), and 207 +/−96 mm³ (25 mg/kg BIWI 1), respectively. The average tumor volume of each group during the observation period is shown in FIG. 5. The initial tumor volume doubling time of the control tumors was approximately 5 days. In animals treated with 25 mg/kg BIWI 1, all tumors responded completely and disappeared around day 22 after start of treatment. No tumor regrowth was observed until the end of the observation period (day 64). Tumors treated with 12.5 mg/kg or 6.25 mg/kg responded completely in ⅚ cases in each dose group, and 4 animals of each group stayed tumor free until the end of the experiment. These results show that BIWI 1 induces excellent anti-tumor responses in MDA-MB 453 xenografted nude mice when given once a week over a period of four weeks, with complete and long-lasting responses from 6.25 mg/kg BIWI 1 to 25 mg/kg BIWI 1.

The present invention is not to be limited in scope by the exemplified embodiments, which are intended as illustrations of single aspects of the invention. Indeed, various modifications of the invention in addition to those shown and described herein will become apparent to those skilled in the art from the foregoing description and accompanying drawings.

All patents and publications cited herein are incorporated by reference in their entirety.

What is claimed is:

1. A conjugate of a CD44v6 specific antibody molecule and a maytansinoid wherein the antibody molecule comprises at least one light chain having the amino acid sequence SEQ ID NO:4 or SEQ ID NO:8, and at least one heavy chain having the amino acid sequence SEQ ID NO:6.

2. The conjugate of claim 1, wherein the antibody molecule is specific for an epitope within the amino acid sequence SEQ ID NO:3.

3. The conjugate of claim 1, wherein the antibody molecule is the monoclonal antibody VFF-18 (DSM ACC2174).

4. The conjugate of claim 1, wherein the antibody molecule is a recombinant antibody having the complementary determining regions (CDRs) of VFF-18.

5. The conjugate of claim 1, wherein the antibody molecule comprises two light chains each light chain having the amino acid sequence SEQ ID NO:4 or SEQ ID NO:8, and two heavy chains each heavy chain having the amino acid sequence SEQ ID NO:6.

6. The conjugate of any one of claims 1 to 5, wherein the maytansinoid is linked to the antibody molecule by a disulfide moiety.

7. A conjugate of a CD44v6 specific antibody molecule and a maytansinoid, wherein the antibody molecule comprises at least one light chain having the amino acid sequence SEQ ID NO:4 or SEQ ID NO:8, and at least one heavy chain having the amino acid sequence SEQ ID NO:6, wherein the maytansinoid has the formula:

Formula (IV)

8. The conjugate of claim 7, wherein the antibody molecule is specific for an epitope within the amino acid sequence SEQ ID NO:3.

9. The conjugate of claim 7, wherein the antibody molecule is the monoclonal antibody VFF-18 (DSM ACC2174).

10. The conjugate of claim 7, wherein the antibody molecule is a recombinant antibody having the complementary determining regions (CDRs) of VFF-18.

11. The conjugate of claim 7, wherein the antibody molecule comprises two light chains each light chain having the amino acid sequence SEQ ID NO:4 or SEQ ID NO:8, and two heavy chains each heavy chain having the amino acid sequence SEQ ID NO:6.

12. A conjugate of a CD44v6 specific antibody molecule and a maytansinoid, wherein the antibody comprises at least one light chain having the amino acid sequence SEQ ID NO:4, and at least one heavy chain having the amino acid sequence SEQ ID NO:6, and wherein the maytansinoid has the formula:

(Formula IV)

and is linked to the antibody through a disulfide bond.

13. The conjugate of any one of claims 7 to 12, wherein one or more maytansinoid residues are linked to an antibody molecule.

14. The conjugate of claim 13, wherein 3 to 4 maytansinoid residues are linked to an antibody molecule.

15. The conjugate of any one of claim 7 to 12, wherein the maytansinoid is linked to the antibody molecule through a —S—$CH_2CH_2$—CO—, a —S—$CH_2CH_2CH_2CH_2$—CO—, or a S—$CH(CH_3)CH_2CH_2$—CO— group.

16. A pharmaceutical composition comprising a conjugate according to any one of claims 1 to 5, and a pharmaceutically acceptable carrier, diluent, or excipient.

17. A pharmaceutical composition comprising a conjugate according to any one of claims 7 to 12, and a pharmaceutically acceptable carrier, diluent, or excipient.

18. A method of treatment of cancer in a patient in need thereof comprising administering to the patient a therapeutically effective amount of a conjugate according to any one of claims 1 to 5.

19. A method of treatment of cancer in a patient in need thereof comprising administering to the patient a therapeutically effective amount of a conjugate according to any one of claims 7 to 12.

20. The method of claim 18, wherein the cancer is selected from the group consisting of head and neck squamous cell carcinoma, esophagus squamous cell carcinoma, lung squamous cell carcinoma, skin squamous cell carcinoma, cervix squamous cell carcinoma, breast adenocarcinoma, lung adenocarcinoma, pancreas adenocarcinoma, colon adenocarcinoma, and stomach adenocarcinoma.

21. The method of claim 19, wherein the cancer is selected from the group consisting of head and neck squamous cell carcinoma, esophagus squamous cell carcinoma, lung squamous cell carcinoma, skin squamous cell carcinoma, cervix squamous cell carcinoma, breast adenocarcinoma, lung adenocarcinoma, pancreas adenocarcinoma, colon adenocarcinoma, and stomach adenocarcinoma.

* * * * *